(12) United States Patent
Hibst et al.

(10) Patent No.: US 7,071,363 B2
(45) Date of Patent: Jul. 4, 2006

(54) STRUCTURED CATALYST BED

(75) Inventors: Hartmut Hibst, Schriesheim (DE); Sebastian Storck, Mannheim (DE); Dirk Demuth, Nussloch (DE); Wolfram Stichert, Heidelberg (DE); Jens Klein, Heidelberg (DE); Stephan A. Schunk, Heidelberg (DE); Andreas Sundermann, Heidelberg (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 234 days.

(21) Appl. No.: 10/617,859

(22) Filed: Jul. 14, 2003

(65) Prior Publication Data

US 2004/0019240 A1      Jan. 29, 2004

(30) Foreign Application Priority Data

Jul. 15, 2002   (DE)   ................. 102 31 976

(51) Int. Cl.
  *C07C 45/00*   (2006.01)
  *B01J 23/48*   (2006.01)
  *B01J 23/50*   (2006.01)
(52) U.S. Cl. ................. 568/476; 568/483; 502/347
(58) Field of Classification Search ............. 568/476, 568/483; 502/347
  See application file for complete search history.

(56) References Cited

U.S. PATENT DOCUMENTS

| | | | |
|---|---|---|---|
| 4,925,986 A | 5/1990 | Monnier et al. | ............. 568/450 |
| 4,925,987 A | 5/1990 | Monnier et al. | ............. 568/450 |
| 4,942,263 A | 7/1990 | Monnier et al. | ............. 568/476 |

FOREIGN PATENT DOCUMENTS

EP      326392      3/1994

OTHER PUBLICATIONS

Weissermel et al., *Ind. Org. Chem.*, 1998, pp. 123, 124, 204.
Haber et al., *Bull. Acad. Pol.Sci., Ser. Sci. Chem.*, 29, 1983, 563.
Haber et al., *Catal. Letters*, 9, 1991, 297.
Morselli et al., *J. Catal.*, 75, 1982, 112.
Popova et al., *Kinetics & Catalysis*, 6, 1965, 856.
Srednev et al., *Russ. J.Org.Chemie*, 34, 1998, 968.

*Primary Examiner*—Sikarl A. Witherspoon
(74) *Attorney, Agent, or Firm*—Novak Druce & Quigg LLP; Jason D. Voight

(57) ABSTRACT

The invention relates to a novel structured catalyst bed which optionally comprises at least one part bed comprising at least one catalytically active mixture of oxides of the main group metals and transition metals and additionally comprises at least one catalytically active part bed comprising at least silver, at least one alkali metal and a porous support material and finally and necessarily at least one catalytically active part bed comprising at least one alkali metal phosphate and at least one sheet silicate.

10 Claims, 3 Drawing Sheets

STRUCTURED CATALYST BED

The invention relates to a novel structured catalyst bed which optionally comprises at least one part bed comprising at least one catalytically active mixture of oxides of the main group metals and transition metals and additionally comprises at least one catalytically active part bed comprising at least silver, at least one alkali metal and a porous support material and finally and necessarily at least one catalytically active part bed comprising at least one alkali metal phosphate and at least one sheet silicate.

Furthermore, the present invention relates to a process for preparing crotonaldehyde from $C_4$-monoolefins or -diolefins using this structured catalyst bed.

An embodiment of the present invention provides a process for the direct synthesis of crotonaldehyde, which comprises the following reaction steps:

(1) dehydrogenation of butene to 1,3-butadiene
(2) epoxidation of 1,3-butadiene to 1,2-epoxy-3-butene (vinyloxirane)
(3) isomerization of 1,2-epoxy-3-butene to 2-butenal (crotonaldehyde).

In the present patent application, "butadiene" is the $C_4$-diolefin 1,3-butadiene, "vinyloxirane" is 1,2-epoxy-3-butene and "crotonaldehyde" is 2-butenal.

In the present process, step (1) is optional if butadiene and not butene is to be used as starting material.

The prior art relating to each individual reaction step and possible combinations is described below.

The dehydrogenation of butene, i.e. the reaction (1), can be carried out, for example, by the Dow process with addition of steam [cf., for example, B. K. Weissermel, H.-J. Arpe in: *Industrielle Organische Chemie*, 5$^{th}$ Edition (1998), 123]. Here, a butadiene selectivity of about 90% is achieved at a conversion of about 50% using a Ca—Ni phosphate catalyst stabilized with chromium oxide at from 600 to 675° C. An alternative process is oxydehydrogenation, as has been implemented, for example, by PetroTex using a heterogeneous catalyst comprising a ferrite of the metals Zn, Mn or Mg. The addition of oxygen not only effects subsequent combustion of hydrogen but also initiates the dehydrogenation by abstraction of hydrogen from the allyl position [cf.

K. Weissermel, H.-J. Arpe in: *Industrielle Organische Chemie*, 5$^{th}$ Edition, (1998), 124].

A two-stage synthesis of crotonaldehyde from butene (circumventing the formation of vinyloxirane) has been described in a number of studies by J. Haber and colleagues [cf., for example, J. Haber and T. Wiltowski, *Bull. Acad. Pol. Sci., Ser. Sci. Chim.* 29 (1983), 563, J. Haber and M. Witko, *Catal. Letters* 9 (1991) 297]. The catalyst used here is based on copper molybdates ($CuMoO_4$) and alters its composition during the course of the reaction. If pure butene is passed over the catalyst, monovalent copper molybdates are formed, with "$Cu_2Mo_3O_{10}$" promoting he isomerization of butene to butadiene and "$Cu_6Mo_4O_{15}$" leading, at selectivities of up to 70%, to insertion of oxygen and thus to formation of crotonaldehyde. However, these reactions are all carried out in non-steady-state operation, i.e. using gas pulses which are introduced into an inert gas stream. Thus, for example starting material shots in the milliliter range are injected into a stream of He by means of a syringe. This stream is-then passed over a catalyst. However, no teachings are provided in the abovementioned documents as to how such a reaction is carried out under the steady-state conditions important in industrial practice.

Morselli et al. achieve an 80 mol % selectivity for the conversion of butene into crotonaldehyde (which is obtained as by-product in addition to furan and maleic acid) at a conversion of 25%, once again under non-steady state experimental conditions, i.e. using a pulsed micro reactor [cf. Morselli et al., *J. Catal.* 75 (1982), 112]. The authors use a vanadium-phosphorus oxide catalyst for this purpose. The feed gas does not contain any oxygen. Here too, there is the disadvantage that non-steady-state conditions are unsuitable for large-scale industrial applications.

The best selectivities for the conversion of n-butenes into crotonaldehyde under steady-state conditions have been published by Popova et al. [N. I. Popova and F. A. Mil'man, *Kinetics & Catalysis* 6 (1965) 856; translation of the Russian edition]. Cu oxide/$SiO_x$ catalysts are used in the study. The selectivities of 16 mol % reported there although achieved at very low conversions, are the best selectivities obtained according to the prior art when oxygen is used in the feed gas. However, both the selectivity and, in particular, the low conversion mean that the process described in this publication is not suitable for (large-scale) industrial use, With regard to reaction (2), i.e. the conversion of butadiene into vinyloxirane, mention should be made of EP-A 0 326 392 (Selective epoxidation of olefins. Eastman Kodak) This describes, inter alia, use of an oxygen-containing gas in the presence of silver-containing catalysts in a temperature range from 75 to 325° C. for the conversion of 1,3-butadiene into vinyloxirane and achieves conversions in the range from 0.1 to 75%. No teachings are provided in respect of a fiber reaction of the vinyloxirane to form crotonaldehyde, but instead the document is directed explicitly only at the provision of catalytic processes for the epoxidation of olefins having longer chains than ethylene.

With regard to the direct conversion of butadiene into crotonaldehyde, i.e. the combination of reactions (2) and (3), mention may be made of U.S. Pat. No. 4,942,263. This publication by Eastman Kodak claims a process for the direct preparation of crotonaldehyde from 1,3-butadiene and oxygen. Metallic silver on a substrate having a surface area of at least 50 $m^2/g$ is claimed as catalyst. A disadvantage of this process of the prior art is, in particular, that only extremely small conversions of less than 1% are achieved (see comparative discussion below).

A summary finally needs to be given of the prior art regarding the reaction (3), i.e. the isomerization of 1,2-epoxy-3-butene to crotonaldehyde. In this context, Eastman Kodak has likewise published two patents: (1) U.S. Pat. No. 4,925,986. Some alkali metal, alkaline earth metal and transition metal halides are claimed here as catalyst; (2) U.S. Pat. No. 4,925,987. In this patent, binary and mixed metal oxides of groups Ib and IIb are claimed as: catalyst. The use of $Li_3PO_4$ is not disclosed in these two documents. The conversion of vinyloxirane into crotonaldehyde over $Li_3PO_4$ in a liquid solvent phase (hexane) has, been described by. Srednev et al. [Russ. *J. Org. Chem.* 34,(1998), 968]. However, no teachings are provided in respect of a corresponding reaction in the gas phase.

In summary, the prior art thus does not disclose any steady-state process for the direct synthesis of crotonaldehyde from butadiene or from butadiene which proceeds at conversions relevant for large-scale industrial applications. Owing to the disadvantages summarized here of processes going via butadiene and/or vinyloxirane, crotonaldehyde is up to now produced not by this route but by, for example, dimerization and dehydration of acetaldehyde (aldol condensation), batchwise in the liquid phase [cf., for example, B. K. Weissermel, H.-J. Arpe in: *Industrielle Organische Chemie*, 5<sup>th</sup> Edition (1998), p. 204].

It is an object of the present invention to provide a novel catalyst which can be used, in particular, for the direct synthesis of crotonaldehyde from butene or from butadiene. The object of the present invention fisher comprises provision of a process using the catalyst in question with this catalyst preferably being able to be used inexpensively in a fixed-bed reactor, i.e. under steady-state conditions, and making it possible to achieve conversions which are above the conversions obtained according to the prior art.

We have found that this object is achieved by a novel, structured catalyst bed which can, for example, be instilled in a fixed-bed reactor so as to make a steady-state reaction possible

DETAILED DESCRIPTION OF THE INVENTION

An advantage of the catalyst bed claimed according to the present invention is that it opens up a way of continuously converting $C_4$-monoolefins or -diolefins into crotonaldehyde in yields of greater than 1% in a single fixed-bed reactor.

The use of the catalyst bed of the present invention is described by way of example for the direct synthesis of crotonaldehyde from butene or butadiene. However, this does not mean that the novel material. i.e. the structured catalyst bed, could not also be used for any other reactions.

Figure 1:
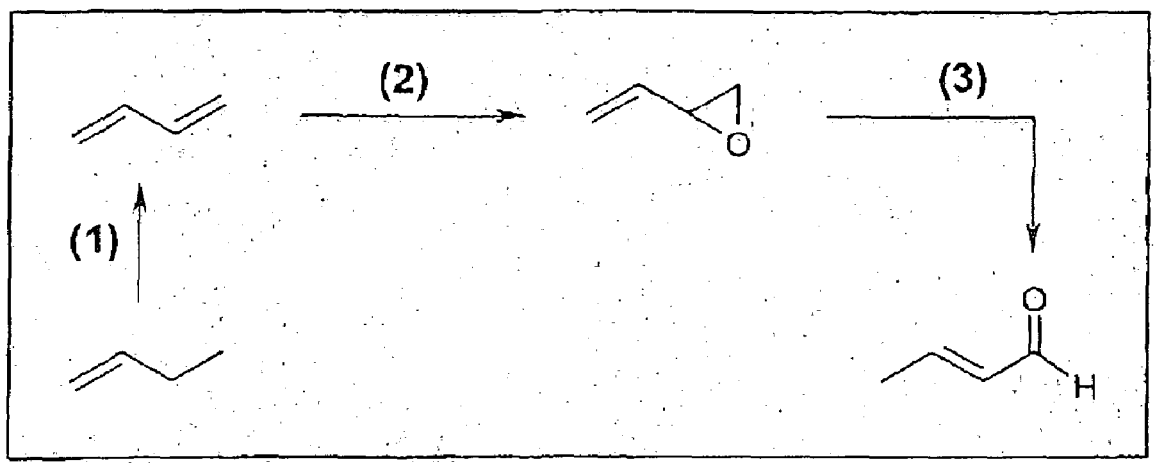
FIG 1 shows an example of the various part reactions and the chemical formula of the main products and starting materials of the reaction.

The various part reactions and the chemical formulae of the main products and starting materials of the reaction being described by way of example are shown schematically in FIG. 1.

Figure 2:
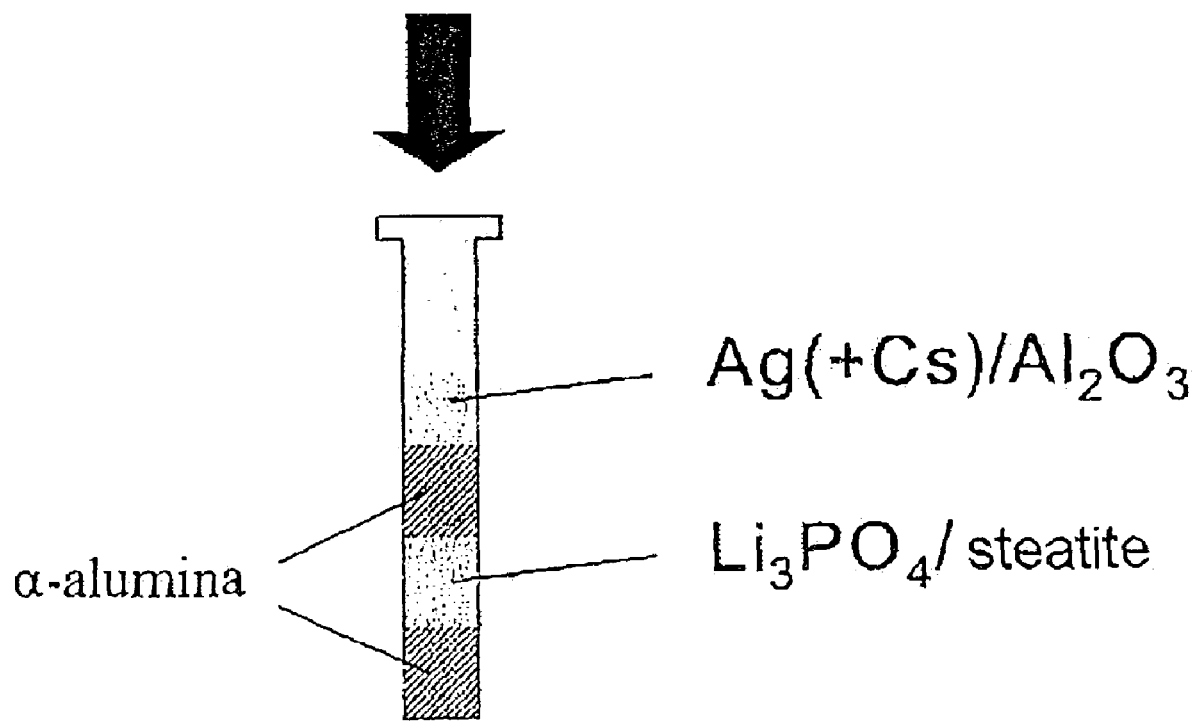
FIG. 2 shows a two-part catalyst bed as is used when butadiene is the starting material, i.e. when reaction step (1) is omitted.

The individual part reactions or reaction steps are, as indicated above:

(1) dehydrogenation of butene to 1,3-butadiene
(2) epoxidation of 1,3-butadiene to 1,2-epoxy-3-butene (vinyloxirane)
(3) isomerization of 1,2-epoxy-3-butene to 2-butenal (crotonaldehyde), FIG. 2 shows a two-part catalyst bed as is used when butadiene is the starting material, i.e. when reaction step (1) is omitted.

The part bed (II) for reaction step (2) comprises at least one catalytically active material and is denoted schematically as "Ag(+Cs)/$Al_2O_3$" in FIG. 2. Suitable catalytically active materials for this part bed are in principle all catalysts which promote the part reaction (2) in terms of selectivity and/or conversion. In a preferred embodiment, the catalyst of this part bed (II) comprises at least silver and at least one alkali metal and is applied to at least one porous support. Suitable porous supports are all materials known to those skilled in the art which have at least micropores or mesopores. Examples which may be mentioned here are: aluminum oxides, activated aluminum oxides, silicates, silica, kieselguhr, water glass, clays, corundums metal oxides, zeolites or mixtures of at least two of the above mentioned substances. The composition Ag with an alkali metal on α-aluminum oxide is particularly preferred. Furthermore, a ratio of Ag/alkali metal of from 1000:1 to 5000:1 is particularly preferred. An Ag loading on the support material of from 1% by weight to 5% by weight is likewise particularly preferred. The part bed can comprise her additives or auxiliaries in addition to the catalyst.

The part bed (III) for step (3) which comprises at least one catalytically active material, is denoted summarily as "$Li_3PO_4$/steatite" in FIG. 2. As catalytically active material for this part bed, it is in principle possible to use any catalyst known to those skilled in the art which promotes ring opening. Alkali metal phosphates are preferred here and $Li_3PO_4$ is particularly preferred. As support it is in principle possible to use any sheet silicate, with particular preference being given to talc in any modification (soapstone, steatite).

Between the catalysts and optionally also before and/or after the first/last active bed, it is possible, as an option, to install a not necessarily catalytically active intermediate bed of porous material which in principle has to satisfy two boundary conditions: (i) the material has to be sufficiently permeable to gas and (ii) it should counter backmixing of starting Materials and/or products. In this context, all porous materials which are known to those skilled in the art and have been mentioned above ale conceivable in principle. The use of α-alumina is particularly preferred for the purposes of the present invention.

The one or more not necessarily catalytically active intermediate bed(s) is located in at least one position within the structured catalyst bed, with this position being selected from the following group: (i) before the first catalytically active part bed in the direction of the feed gas flow, (ii) between at least one pair of catalytically active part beds and (iii) after the last catalytically active part bed in the direction of the feed gas flow, It is also conceivable for a free gas space to be present between and/or before and/or after a catalytically active part bed.

In a preferred embodiment, these various part beds are charged one after the other in a tube reactor and/or a fixed-bed reactor, as shown schematically in FIG. 2. The thickness of the individual layers needs to be such that steady-state operation is made possible, i.e. a feed gas stream can be introduced continuously and the stream comprising the reaction product in the present case crotonaldehyde can then be taken off at the other end. In principle, the thickness and/or arrangement of the individual beds are subject to no restrictions as long as continuous conversion of the starting materials into crotonaldehyde is possible and the overall bed is structured according to the present invention. A bed is "structured" when at least one part bed is recognizable or is measurably separated in space from the remainder of the overall bed. The thickness of each layer and the total thickness are to beg matched, in particular, to the space velocity of the gas (GHSV=gas hourly space velocity; the feed gas volume per liter of catalyst and per hour) and to the desired or tolerable pressure drop.

Figure 3:
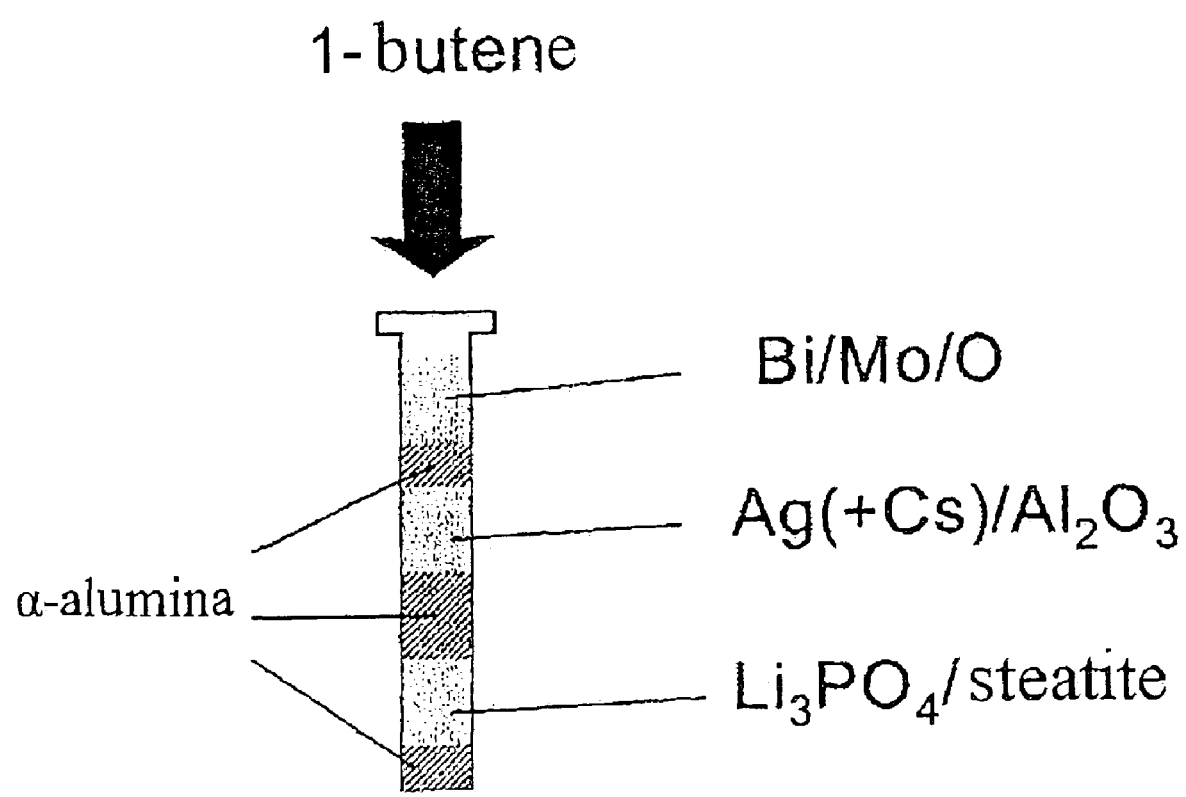
FIG. 3 shows a corresponding three-part catalyst bed as is used when butene is to be used as starting material.

Finally, FIG. 3 shows a corresponding three part catalyst bed as is used when butene is to be used as starting material. As regards the part beds for the steps (2) and (3) and the intermediate beds, what has been written above applies. For the conversion of butene into butadiene, i.e. for step (1), a further part catalyst bed (I) is installed upstream of step (2) in the structured catalyst bed. This part bed comprises at least one catalytically active material comprising at least a mixture of at least two oxides of the main group metals and transition metals. Preference is given to a multiphase system comprising at least molybdenum oxide, bismuth oxide and tungsten oxide in any compositions. In this context, the relevant contents of EP 0 319 754 are fully incorporated by reference into the present text. In a particularly preferred embodiment, an oxide comprising Mo, Bi, W, Co, Fe, Si and K is used, with the composition $Mo_{12}Bi_{1.2}W_{2.4}Co_{4.8}Fe_{0.8}Si_{1.6}K_{0.05}O_x$ being particularly preferred.

As regards the order of the part beds, the catalytically active part beds (I), (II) and (III) and optionally at least one not necessarily catalytically active intermediate bed can in principle be installed in any permutation and repetition or in any permutation or repetition. Furthermore, these part beds are in a preferred embodiment, installed in the order part bed (III) after part bed (II) or part bed (III) after part bed (II) after part bed (I) in the flow direction of the feed gas.

Furthermore, although the part beds are located in a common (tube) reactor, preference is given to process parameters, in particular temperature and/or pressure and/or pressure drop, etc., being able to be regulated individually for each part bed. In the case of temperature, this can be achieved, for example, by means of various heating elements wound around the tube reactor.

The yield and selectivity achieved by way of example, by means of the catalyst bed of the present invention can be compared to the corresponding values obtainable according to the prior art. Thus, for example, U.S. Pat. No. 4,942,263 discloses results for the preparation of crotonaldehyde form 1,3-butadiene. At a reaction temperature of 225° C. and a GHSV of 2400 h$^{-1}$, selectivities to crotonaldehyde of 60% were able to be achieved at conversions of 0.03% and a feed composition of 50% of butadiene in $O_2$ (yield: 0.018%).

However, the values reported appear to be subject to large uncertainties, since the error range for the selectivities becomes very large at the low conversions in question. In the document, it is concluded from the data that the high surface area of the support material results in high selectivities to crotonaldehyde. This conclusion does not appear to be adequately supported by the data. Even when this is disregarded, the yields to crotonaldehyde (or the corresponding conversions) described in this document are significantly worse than the yields found in the case of the present invention (see examples).

Analogously, the yields of crotonaldehyde in the above-discussed publication by Popova et al. are low, particularly in comparison to example 3 discussed below using the catalyst bed of the present invention. Popova et al. discuss the preparation of crotonaldehyde from 1-butene using Cu-based catalysts. At 370° C. and a GHSV of 8000 h$^{-1}$, a selectivity to crotonaldehyde of 16% is achieved at a composition of the gas stream of 4:1:5 (butene: $O_2:N_2$) and a conversion of 15% (yield: 0:24%). As catalyst, 0.5% of Cu on $SiO_2$ was utlized. The main product here was methyl vinyl ketone (50–60% selectivity) and the product relevant to the present invention, viz, crotonaldehyde, is only a by-product.

The invention is illustrated below with the aid of selected examples. These expressly do not restrict the general validity of the subject matter of the present invention.

EXAMPLE 1

Conversion of 1,3-butadiene into Crotonaldehyde Using the Two-Part Catalyst Bed of the Present Invention The reaction of 1,3-butadiene to form crotonaldehyde was carried out using a bed structured according to the present invention and comprising 1) Ag(+Cs)/α-$Al_2O_3$ and 2) $Li_3PO_4$/steatite. The steatite is present as granules having a particle size of from 2 to 3 mm. The bed was, as in all other examples mentioned here, placed in a tube reactor (8 mm diameter). On the basis of the formulae known to those skilled in the art for selectivity, yield and conversion and using the analytical data from a Hewlett Packard HP 5 gas chromatography a selectivity to crotonaldehyde of 29.3% and a conversion of 64.2% were achieved at 250° C., a space velocity of the gas GHSV =6000 h$^{-1}$ and a feed comprising 1% of butadiene in air (yield: 18.8%). This result is based on a catalyst bed having a two-part structure. $Li_3PO_4$, α-alumina and Ag/$Al_2O_3$ were arranged one above the other in a volume ratio of 1:1:1 in a fixed-bed reactor (cf. FIG. 2).

The first part of the bed comprises a catalyst comprising; 2.5% of Ag and 0.001% of Cs on an α-$Al_2O_3$ support. The precipitation of silver was carried out as described below using $Ag_2O$, ethanolamine and ethylene diamine. The Cs solute was CsCl, and the $Al_2O_3$ comes from Ceramtec (No. 80411). The second part of the bed comprises 25% of $Li_3PO_4$ (Aldrich) with binder (kaolin) on steatite (Ceramtec, leached). The preparation of this catalyst is likewise described below.

Preparation of Ag/$Al_2O_3$ (Analogous to U.S. Pat. No. 4,356,312)

The $Al_2O_3$ support was impregnated with Ag as amine complex. To prepare the Ag-amine complex, 25.2 g of $H_2C_2O_4×2H_2O$, 24 g of ethylenediamine and 46.35 g of $Ag_2O$ were dissolved in succession in 100 ml of $H_2O$. 6.8 g of ethanolamine were added as reducing agent/solubilizer. This solution was mixed with CsCl so as to give an Ag/Cs ratio of 2500:1. An α-$Al_2O_3$ support (Ceramtec No. 80411) was impregnated with the above-described solution so as to give an Ag loading of 2:5% by weight. Immediately after the preparation had been concluded, the sample was heated to 290° C. over a period of 1 hour in a stream of air (1 l/min) and maintained at this temperature for a further three hours.

Preparation of the $Li_3PO_4$/Steatite Bed

For the preparation of the $Li_3PO_4$/steatite bed, 25 ml of $HNO_3$ (10% strength) were firstly placed in a precipitation vessel, after which first the kaolin (Dorfner) and then $Li_3PO_4$ (Aldrich) were weighed in while stirring. The precipitation suspension was then applied to 89 g of NaOH-leached steatite from Ceramtec. The steatite spheres were placed in a thin layer in porcelain dishes and kept in motion by means of a shaker during the addition of the metal salt solutions. 25% by weight of $Li_3PO_4$ were applied to steatite. The sample was finally dried at 80° C. for 16 hours.

EXAMPLE 2

Conversion of 1,3-butadiene into Crotonaldehyde

In the reaction of 1,3-butadiene to form crotonaldehyde over a two-part bed comprising 1) Ag/α-$Al_2O_3$ and 2) $Li_3PO_4$/steatite, a selectivity to crotonaldehyde of 35.8% was achieved at a conversion of 39.1% (yield: 14.0%). Reaction conditions here were 225° C., a GHSV of 6000 h$^{-1}$ and a feed comprising 1% of butadiene in air. $Li_3PO_4$, α-alumina and Ag/$Al_2O_3$ were arranged one above the other in a volume ratio of 1:1:1 in a fixed-bed reactor. The first part of the catalyst bed comprised a catalyst comprising 5% of Ag on an α-$Al_2O_3$ support (as described in Example 1). The $Al_2O_3$ comes from Ceramtec (No. 80411). The second part of the catalyst bed comprised 25% of $Li_3PO_4$ (Aldrich) with binder (kaolin) on steatite (Ceramtec, leached). Its preparation is likewise described in example 1.

EXAMPLE 3

Conversion of 1-butene into Crotonaldehyde Using the Three-Part Catalyst Bed According to the Present Invention.

In this reaction, a conversion of 59% and a selectivity to crotonaldehyde of 17.9% were achieved over a three-part bed comprising 1) $Mo_{12}Bi_{1.2}W_{2.4}Co_{4.8}Fe_{0.8}Si_{1.6}K_{0.05}O_x$ 2) $Ag(+K)/\alpha$-$Al_2O_3$ and $3Li_3PO_4$/steatite at 300° C., a GHSV of 6000 $h^{-1}$ and using 1% of butene in air as feed (yield=10.6%). To produce the catalyst bed, $Li_3PO_4$, $\alpha$-alumina, $Ag/Al_2O_3$, $\alpha$-alumina again and finally a Bi/Mo/O catalyst were arranged one above the other in a volume ratio of 1:1:1:0.5:1 in a fixed-bed reactor.

The $Mo_{12}Bi_{1.2}W_{2.4}Co_{4.8}Fe_{0.8}Si_{1.6}K_{0.05}O_x$ catalyst was prepared using the method described in EP 319 754 of BASF AG. The catalyst of the second part bed comprised 0.5% of Ag and 0.001% of K on an $\alpha$-$Al_2O_3$-support. The preparation of this catalyst is described in example 1 25% of $Li_3PO_4$ (Aldrch) with binder (kaolin) on steatite (Ceramtec, leached) was once again used for the third part bed and reference may again be made to example 1 for the preparation of this catalyst.

A summary of the selectivities (to crotonaldehyde, CRA) and conversions reported in examples 1 to 3 and in U.S. Pat. No. 4,942,263 ("Kodak") and in the publication by Popova et al ("Popova"; see discussion of the prior art) is given in the following table:

|  | Feed | Catalyst | Temp. [° C.] | GHSV [$h^{-1}$] | Conv. [%] | Selectivity (CRA) [%] |
|---|---|---|---|---|---|---|
| Ex. 1 | 1% of butadiene in air | Ag(+Cs)$Al_2O_3$ + $Li_3PO_4$/steatite | 250 | 6000 | 64.2 | 29.3 |
| Ex. 2 | 1% of butadiene in air | Ag/$Al_2O_3$ + $Li_3PO_4$/steatite | 225 | 6000 | 39.1 | 35.8 |
| Ex. 3 | 1% of 1-butene in air | Mo/Bi/W/Co/Fe/ in Si/K/O + Ag(+K)/$Al_2O_3$ + $Li_3PO_4$/steatite | 300 | 6000 | 59.0 | 17.9 |
| Kodak | 50% of butadiene in $O_2$ | Ag/$Al_2O_3$ | 225 | 2400 | 0.03 | 60 |
| Popova | 40% of 1-butene, 10% of $O_2$, 50% of $N_2$ | Cu/$SiO_2$ | 370 | 8000 | 1.5 | 16 |

We claim:

1. A structured catalyst bed which comprises at least the following part beds: (II) at least one catalytically active part bed comprising at least silver, an alkali metal and a porous support material; and (III) at least one catalytically active part bed comprising at least one alkali metal phosphate and at least one sheet silicate.

2. A structured catalyst bed as claimed in claim 1, which further comprises the following part bed:

(I) at least one catalytically active part bed comprising at least a mixture of oxides of the main group metals and transitions metals.

3. A structured catalyst bed as claimed in claim 1, wherein the part beds are installed in the order part bed (III) after part bed (II) or part bed (III) after part bed (II) after part bed (I) in the flow direction of the feed gas.

4. A structured catalyst bed as claimed in claim 1 which comprises a not necessarily catalytically active intermediate bed or a gas-free intermediate space which is present in at least one position within the structured catalyst bed, with this position being selected from the following group: (i) before the first catalytically active part bed in the direction of the feed gas flow, (ii) between at least one pair of catalytically active part beds and (iii) after the last catalytically active part bed in the direction of the feed gas flow.

5. A structured catalyst bed as claimed in claim 2, wherein the catalytically active part beds (I), (II) and (III) and optionally at least one not necessarily catalytically active intermediate beam are installed in any permutation and repetition.

6. A structured catalyst bed as claimed in claim 1, wherein the catalytically active part bed (II) comprises Ag together with an alkali metal on $\alpha$ aluminum oxide.

7. A structured catalyst bed as claimed in claim 2, wherein the catalytically active part bed (I) comprises at least one mixture of at least two oxides of the main group metals and transition metals.

8. A process for preparing crotonaldehyde from $C_4$-monoolefins or -diolefins in steady-state operation using the structured catalyst bed as claimed in claim 1.

9. A process as claimed in claim 8, wherein butadiene is used in the feed stream and the following two reactions are catalyzed by the part beds (II) and (III), respectively:

(2) epoxidation of butadiene to vinyloxirane;

(3) isomerization of vinyloxirane to crotonaldehyde.

10. A process as claimed in claim 9, wherein butene is used in the feed stream and, in addition to the reactions specified in claim 9, the following reaction is catalyzed by a part bed (I) comprising at least a mixture of oxides of the main group metals and transitions metals:

(1) dehydrogenation of butene to butadiene.

* * * * *